(12) United States Patent
Wijesuriya et al.

(10) Patent No.: US 11,724,045 B2
(45) Date of Patent: Aug. 15, 2023

(54) CONNECTION OF A STOPPER AND PISTON IN A FLUID DELIVERY DEVICE

(71) Applicant: MEDTRONIC MINIMED, INC., Northridge, CA (US)

(72) Inventors: Amith Wijesuriya, Los Angeles, CA (US); Ryan A. Peck, Los Angeles, CA (US); Thomas P. Miller, Porter Ranch, CA (US); Burke K. Chan, Pasadena, CA (US); Victor A. Sanchez, Chatsworth, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 935 days.

(21) Appl. No.: 16/547,507

(22) Filed: Aug. 21, 2019

(65) Prior Publication Data

US 2021/0052828 A1 Feb. 25, 2021

(51) Int. Cl.
*A61M 5/50* (2006.01)
*A61M 5/145* (2006.01)
*A61M 5/172* (2006.01)

(52) U.S. Cl.
CPC ........ *A61M 5/5086* (2013.01); *A61M 5/1454* (2013.01); *A61M 5/172* (2013.01); *A61M 2205/0272* (2013.01); *A61M 2205/18* (2013.01)

(58) Field of Classification Search
CPC ............... A61M 5/5086; A61M 5/172; A61M 2205/0272; A61M 2205/18; A61M 2205/3317; A61M 2205/332; A61M 5/1456; A61M 5/50; A61M 5/145; A61M 5/1452; A61M 5/142; A61M 5/14; A61M 5/168; A61M 2205/0288; A61M 5/178
See application file for complete search history.

(56) References Cited

U.S. PATENT DOCUMENTS

| | | | |
|---|---|---|---|
| 4,562,751 | A | 1/1986 | Nason et al. |
| 4,678,408 | A | 7/1987 | Nason et al. |
| 4,685,903 | A | 8/1987 | Cable et al. |
| 4,755,173 | A | 7/1988 | Konopka et al. |
| 5,080,653 | A | 1/1992 | Voss et al. |
| 5,097,122 | A | 3/1992 | Colman et al. |
| 5,391,250 | A | 2/1995 | Cheney, II et al. |
| 5,485,408 | A | 1/1996 | Blomquist |
| 5,505,709 | A | 4/1996 | Funderburk et al. |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |

(Continued)

*Primary Examiner* — Jason E Flick
(74) *Attorney, Agent, or Firm* — Shumaker & Sieffert, P.A.

(57) ABSTRACT

A device for delivering fluid to a user includes a fluid reservoir for holding the fluid, the fluid reservoir defining an internal volume and a stopper positioned in the internal volume of the fluid reservoir, wherein the stopper is formed with a cavity. The device further includes a piston having a distal end received within the cavity of the stopper and an actuator coupled to the piston for driving the piston into the internal volume of the fluid reservoir. Also, the device includes a coupling device for engaging the piston in the cavity of the stopper at a desired position and a sensor for determining whether the piston is engaged in the cavity of the stopper at the desired position.

20 Claims, 8 Drawing Sheets

(56) References Cited

U.S. PATENT DOCUMENTS

| | | |
|---|---|---|
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 * | 11/2004 | Yap ............... A61M 5/1456 604/152 |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2003/0009133 A1 * | 1/2003 | Ramey ............... A61M 5/1456 604/154 |
| 2007/0123819 A1 | 5/2007 | Mernoe et al. |
| 2010/0160861 A1 | 6/2010 | Causey, III et al. |
| 2021/0196935 A1 * | 7/2021 | Tong ............... A61M 35/10 |

\* cited by examiner

CONNECTION OF A STOPPER AND PISTON IN A FLUID DELIVERY DEVICE

TECHNICAL FIELD

Embodiments of the subject matter described herein relate generally to medical devices. More particularly, embodiments of the subject matter relate to fluid infusion devices such as personal insulin infusion pumps.

BACKGROUND

Portable medical devices are useful for patients that have conditions that must be monitored on a continuous or frequent basis. For example, diabetics are usually required to modify and monitor their daily lifestyle to keep their blood glucose (BG) in balance. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin). In lieu of a syringe, the patient can simply activate the insulin pump to administer an insulin bolus as needed, for example, in response to the patient's high BG level.

A typical infusion pump includes a housing, which encloses a pump drive system, a fluid containment assembly, an electronics system, and a power supply. The pump drive system typically includes a small motor (DC, stepper, solenoid, or other varieties) and drive train components such as gears, screws, and levers that convert rotational motor motion to a translational displacement of a piston that contacts and displaces a plunger or stopper in a reservoir. The fluid containment assembly typically includes the reservoir with the plunger/stopper, tubing, and a catheter or infusion set to create a fluid path for carrying medication from the reservoir to the body of a user. The electronics system regulates power from the power supply to the motor. The electronics system may include programmable controls to operate the motor continuously or at periodic intervals to obtain a closely controlled and accurate delivery of the medication over an extended period.

Typically, systems measure the amount of medication dispensed from, and/or remaining in, the reservoir based on the linear position of the piston. Accordingly, it is desirable to provide devices or methods that ensure accurate measurement of the amount of medication delivered and the amount of medication in the reservoir. Furthermore, other desirable features and characteristics will become apparent from the subsequent detailed description and the appended claims, taken in conjunction with the accompanying drawings and the foregoing technical field and background.

BRIEF SUMMARY

A device for delivering fluid to a user is provided. The fluid delivery device includes a fluid reservoir for holding the fluid, the fluid reservoir defining an internal volume and a stopper positioned in the internal volume of the fluid reservoir, wherein the stopper is formed with a cavity. The device further includes a piston having a distal end received within the cavity of the stopper and an actuator coupled to the piston for driving the piston into the internal volume of the fluid reservoir. Also, the device includes a coupling device for engaging the piston in the cavity of the stopper at a desired position and a sensor for determining whether the piston is engaged in the cavity of the stopper at the desired position.

Also provided is an exemplary embodiment of a device for detecting whether a fluid delivery device stopper is correctly positioned. The detecting device includes a fluid reservoir for holding the fluid, the fluid reservoir defining an internal volume wherein the fluid delivery device stopper is positioned, wherein the stopper is formed with a cavity. The detecting device further includes a piston having a distal end received within the cavity of the stopper and an actuator coupled to the piston for driving the piston into the internal volume of the fluid reservoir. Also, the detecting device includes a sensor for determining whether the piston is engaged in the cavity of the stopper at the desired position.

A method for operating a fluid infusion device is also provided. The method includes holding a fluid in an internal volume of a fluid reservoir partially bounded by a stopper positioned in the internal volume, wherein the stopper is formed with a cavity. The method includes driving a piston into the internal volume of the fluid reservoir and contacting the stopper with the piston. Further, the method includes monitoring a relative position of the stopper in relation to the piston with a sensor to determine whether the stopper moves out of contact with the piston.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to infusion system operation, insulin pump and/or infusion set operation, blood glucose sensing and monitoring, force sensors, signal processing, and other functional aspects of the systems (and the individual operating components of the systems) may not be described in detail here. Examples of infusion pumps and/or related pump drive systems used to administer insulin and other medications may be of the type described in, but not limited to, U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; and 7,621,893; which are herein incorporated by reference.

The subject matter described here relates to a fluid infusion device of the type used to treat a medical condition of a patient. The infusion device is used for infusing fluid into the body of a user. The non-limiting examples described below relate to a medical device used to treat diabetes (more specifically, an insulin pump), although embodiments of the disclosed subject matter are not so limited. Accordingly, the infused fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like.

In fluid infusion devices, the fluid is typically received within a reservoir and a stopper is advanced into the reservoir to force the fluid through a fluid path to the body of a user. In such devices, a piston is advanced by a measured and precise distance into the stopper to cause the stopper to expel the appropriate amount of fluid. In certain circumstances, the piston and stopper may become disconnected after the piston contacts the stopper. For example, reduced friction between the stopper and the reservoir wall may allow the stopper to slip forward when a translational displacement of the piston ends. Further, hydrostatic forces that may arise from gravity when the pump is held above the infusion site also can cause the stopper to move away from the piston. Therefore, a system that measures liquid dispensed from, or liquid remaining in, the reservoir based on the linear position of the piston may be incorrect. As a result, delivery volume accuracy will suffer.

As described herein, a device and method for delivering fluid to a user are provided with a coupling structure and/or sensing structure for preventing and/or detecting unintended decoupling or separation between the stopper and the piston. As a result, delivery volume accuracy may be improved while reducing the danger of under-dosage or over-dosage to the patient.

Sensors used in the sensing structure may be configured to react in response to force imparted thereto. In this regard, electrical, mechanical, magnetic, and/or other measurable or detectable characteristics of the sensor vary in accordance with the amount of force applied to the sensor. In practice, the sensor might implement or otherwise leverage known sensor technologies, such as the sensor technology described in U.S. Pat. No. 6,485,465. An exemplary sensor includes at least one electrical lead that is electrically coupled to the electronics module (or controller) of the fluid infusion device. Alternatively, the sensor could use wireless data communication technology to provide force-related data to the electronics module. In certain implementations, the sensor is suitably configured to indicate or generate a plurality of different output levels that can be monitored and/or determined by the electronics module. In practice, the output levels obtained from the sensor are initially conveyed as analog voltages or analog currents, and the electronics module includes an analog-to-digital converter that transforms a sampled analog voltage into a digital representation. Conversion of sensor voltage into the digital domain is desirable for ease of processing, comparison to threshold values, and the like.

In particular embodiments, the sensor is realized as an electromechanical component having at least one variable resistance that changes as the force applied to the sensor changes. In alternative embodiments, the sensor is a capacitive sensor, a piezoresistive sensor, a piezoelectric sensor, a magnetic sensor, an optical sensor, a potentiometer, a micromachined sensor, a linear transducer, an encoder, a strain gauge, or the like, and the detectable parameter or characteristic might be compression, shear, tension, displacement, distance, rotation, torque, force, pressure, or the like. In practice, changing characteristics of the sensor are associated with output signal characteristics that are responsive to a physical parameter to be measured. Moreover, the range and resolution of the monitored output signal provides for the desired number of output levels (e.g., different states, values, quantities, signals, magnitudes, frequencies, steps, or the like) across the range of measurement. For example, the sensor might generate a low or zero value when the applied force is relatively low, a high or maximum value when the applied force is relatively high, and intermediate values when the applied force is within the detectable range.

In an exemplary embodiment, the coupling structure includes a first magnetic component and a second magnetic component. Each of these components may produce a magnetic field, or one component may produce a magnetic field while the other component is attracted to the magnetic field. In other words, each component may be a magnet, or one component may be a magnet and one component may be a metal that is attracted to a magnet. One magnetic component is mounted in a recess of the stopper while the other magnetic component is mounted at a distal end of the piston. As a result, when the piston is advanced into a selected position relative to the stopper, the magnetic field between the magnetic components is sufficiently strong to hold together the stopper and piston to prevent unintended separation. When separation is desired, a user may pull the piston from the stopper to overcome the attractive magnetic force. For such an embodiment, the sensor may be a magnetic field sensor configured to monitor a magnetic field near one magnetic component to determine whether the stopper and piston separate from one another.

In another embodiment, the coupling structure includes a cavity or cavities that are formed along an inner sidewall surface and a projection or projections that are formed along the outer side surface of the piston. When the piston is advanced to the selected position relative to the stopper, the projection or projections are received in the cavity or cavities. The projection or projections have sufficient flexural strength to hold together the stopper and the piston after the position is advanced to the selected position. When separation is desired, a user may pull the piston from the stopper to overcome the flexural strength of the projections, causing the projections to bend to allow the piston to be withdrawn from the stopper cavity. For such an embodiment, the sensor may be a pressure or flexural stress sensor configured to monitor pressure or flexural tension in the projection or projections as indicative of whether the stopper and piston separate from one another.

In yet another embodiment, the coupling structure includes a cavity or cavities that are formed along an inner sidewall surface and a projection or projections that are formed along the outer side surface of the piston. In this embodiment, the projection or projections are spring-loaded or otherwise biased to extend outward from the outer side surface of the piston. For example, a spring-loaded ball or balls may be embedded in the outer side surface of the piston. When the piston is advanced to the selected position relative to the stopper, the projection or projections are received in the cavity or cavities. The projection or projections are sufficiently biased to hold together the stopper and the piston after the position is advanced to the selected position. When separation is desired, a user may pull the piston from the stopper to overcome the spring force pushing the projections outward, causing the projections to be retracted into the piston to allow the piston to be withdrawn from the stopper cavity. For such an embodiment, the sensor may be a spring force sensor configured to monitor tension in the biasing element as indicative of whether the stopper and piston separate from one another.

In each embodiment the coupling structure may further include an additional or alternative sensor for determining whether the piston is engaged in the cavity of the stopper at the selected position. For example, the additional or alternative sensor may include two reciprocal sensing components for registering contact therebetween. Specifically, the first sensing components may be a touch pad or similar component that registers contact with another object, such as through electric field proximity sensing or through capacitive sensing. The second sensing component may be a projection configured to contact the first sensing component when the piston contacts or engages the stopper. For example, a projection may be formed on the stopper to extend into the stopper cavity, while a touch pad is formed on the distal end of the piston. When the piston is advanced to the selected position, the projection contacts the touch pad, thereby creating a change in electrostatic force. A further component may monitor or measure electrostatic forces to determine whether the piston is engaged in the cavity of the stopper at the selected position. For each embodiment, the sensor further includes sufficient electronic components to monitor the appropriate property and to communicate when the piston and stopper are engaged and disengaged.

Figure 1:
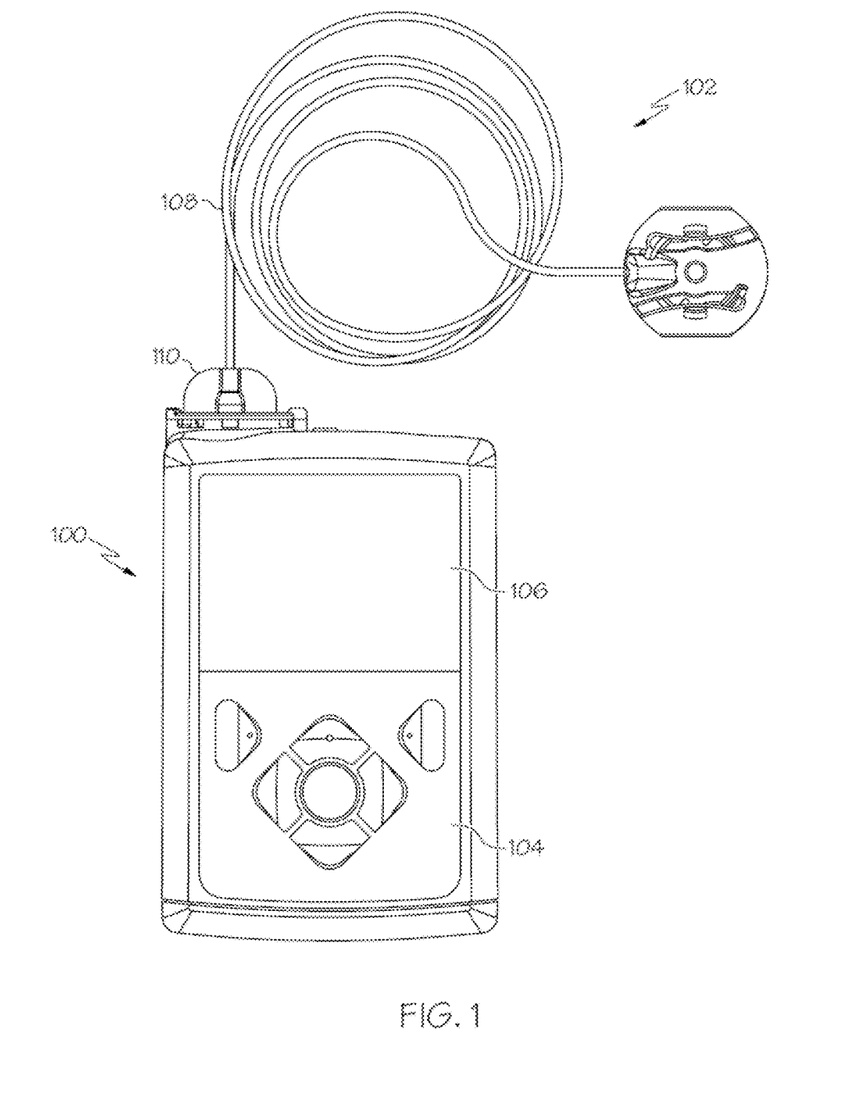
FIG. 1 is a schematic representation of an embodiment of a fluid infusion device.

FIG. 1 is a plan view of an exemplary embodiment of a fluid infusion device 100. FIG. 1 also shows an infusion set 102 coupled to the fluid infusion device 100. The fluid infusion device 100 is designed to be carried or worn by the patient. The fluid infusion device 100 may leverage a number of conventional features, components, elements, and characteristics of existing fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

This embodiment shown in FIG. 1 includes a user interface 104 that includes several buttons that can be activated by the user. These buttons can be used to administer a bolus of insulin, to change therapy settings, to change user preferences, to select display features, and the like. Although not required, the illustrated embodiment of the fluid infusion device 100 includes a display element 106. The display element 106 can be used to present various types of information or data to the user, such as, without limitation: the current glucose level of the patient; the time; a graph or chart of the patient's glucose level versus time; device status indicators; etc. In some embodiments, the display element 106 is realized as a touch screen display element and, therefore, the display element 106 also serves as a user interface component.

The fluid infusion device 100 accommodates a fluid reservoir (hidden from view in FIG. 1) for the fluid to be delivered to the user. A length of tubing 108 is the flow path that couples the fluid reservoir to the infusion set 102. The tubing 108 extends from the fluid infusion device 100 to the infusion set 102, which provides a fluid pathway with the body of the user. A removable cap or fitting 110 is suitably sized and configured to accommodate replacement of fluid reservoirs (which are typically disposable) as needed. In this regard, the fitting 110 is designed to accommodate the fluid path from the fluid reservoir to the tubing 108.

Figure 2:
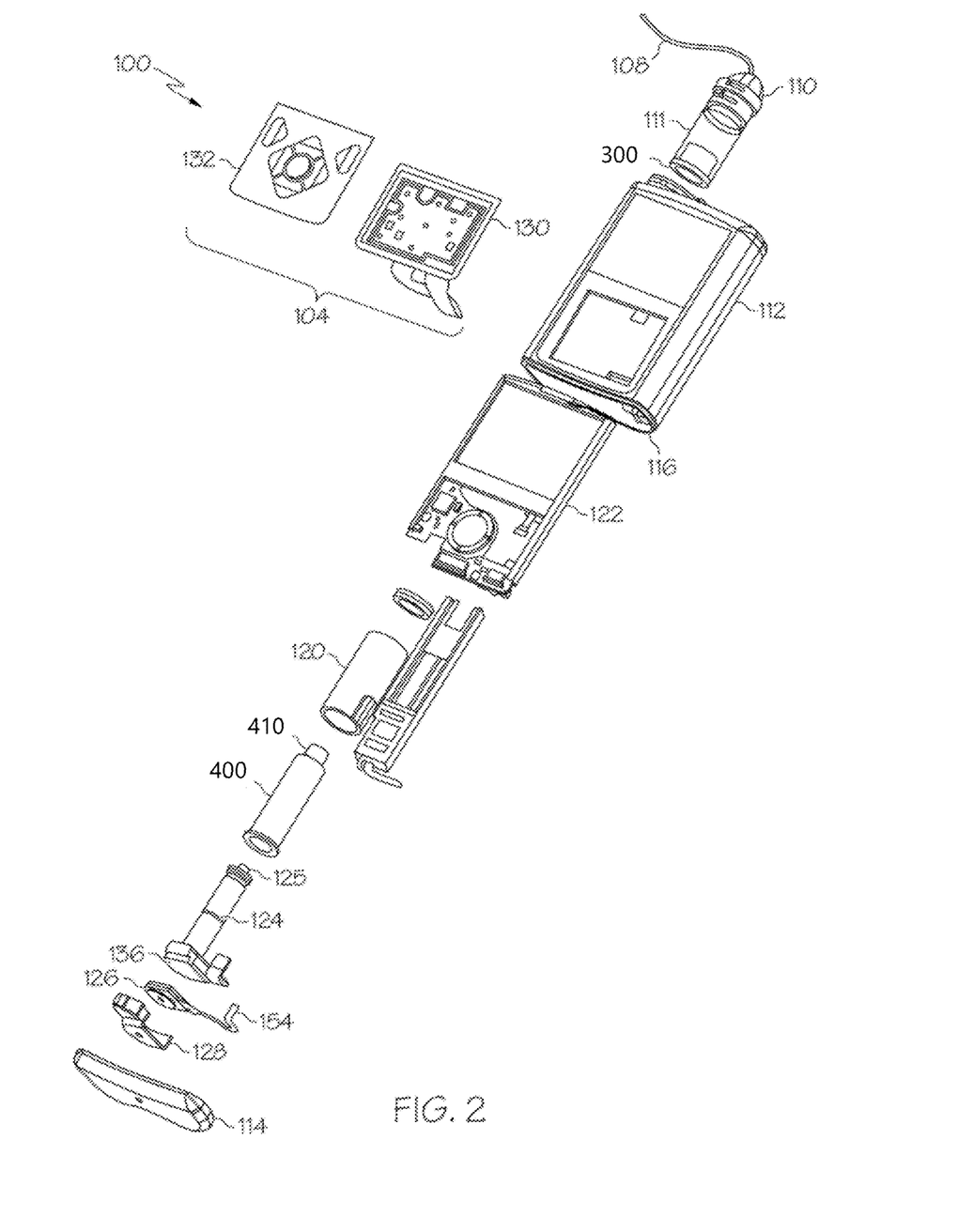
FIG. 2 is an exploded perspective view of the fluid infusion device shown in FIG. 1.

FIG. 2 is an exploded perspective view of the fluid infusion device 100. For the sake of brevity and simplicity, FIG. 2 is a simplified depiction of the fluid infusion device 100 that does not include all of the elements, components, and features that would otherwise be present in a typical embodiment. It should be appreciated that a deployed implementation of the fluid infusion device 100 will include additional features, components, and elements that are not shown in the figures.

The embodiment of the fluid infusion device 100 illustrated in FIG. 2 includes a housing 112 and a housing end cap 114 that is coupled to an end 116 of the housing 112 to enclose components within the housing 112. These internal components include, without limitation: a battery tube sub-assembly 118; a sleeve 120; a slide or piston 400; an electronics assembly 122; a drive motor assembly 124 having a drive screw 125; a force sensor 126; and a motor support cap 128. FIG. 2 also depicts some components that are located outside the housing 112, namely, a keypad assembly 130 and a graphic keypad overlay 132 for the keypad assembly 130. The keypad assembly 130 and the graphic keypad overlay 132 may be considered to be part of the user interface 104 of the fluid infusion device 100. The outer edge of the motor support cap 128 is attached to the interior side of the housing 112, and the motor support cap 128 contacts the force sensor 126 to remove assembly tolerances from the drive motor assembly 124. FIG. 2 also depicts an exemplary fluid reservoir 111, which is inserted into a reservoir cavity defined within the housing 112. The reservoir cavity is configured, sized, and shaped to accommodate fluid reservoirs, and the fluid reservoir 111 is maintained in the reservoir cavity using the fitting 110. The electronics assembly 122 may include a suitably configured electronics module (not shown in FIG. 2), which may include or cooperate with a power supply, at least one memory element, at least one processor, processing logic, and device software, firmware, and application programs.

Figure 3:
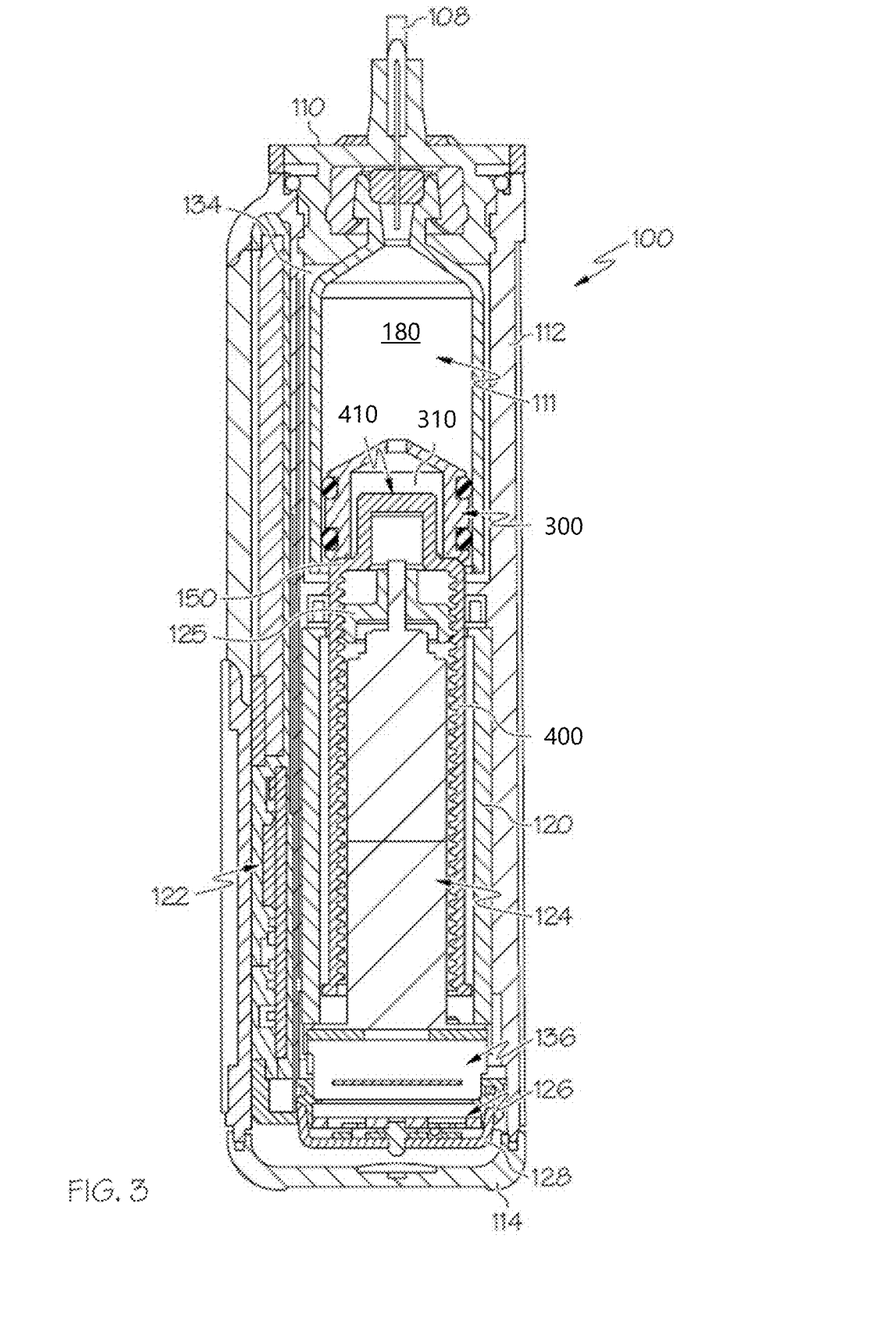
FIG. 3 is a cross sectional view of the fluid infusion device shown in FIG. 1, corresponding to a cross section taken longitudinally through the drive motor assembly and the fluid reservoir.

FIG. 3 is a cross sectional view of the fluid infusion device 100, corresponding to a cross section taken longitudinally through the drive motor assembly 124 and the fluid reservoir 111. FIG. 3 depicts the state of the fluid infusion device 100 after the fluid reservoir 111 has been inserted into the reservoir cavity 134 and after the fitting 110 has been secured to the housing 112 to hold the fluid reservoir 111 in place. While certain embodiments accommodate disposable, prefilled reservoirs, alternative embodiments may use refillable cartridges, syringes or the like. A cartridge can be prefilled with insulin (or other drug or fluid) and inserted into the housing 112. Alternatively, a cartridge could be filled by the user using an appropriate adapter and/or any suitable refilling device.

When assembled as shown in FIG. 3, the drive motor assembly 124 is located in the housing 112. The force sensor 126 is operatively associated with the drive motor assembly 124. For this particular embodiment, the force sensor 126 is coupled to the drive motor assembly 124, and it is located between a base end of the drive motor assembly 124 and the motor support cap 128. In one implementation, the force sensor 126 is affixed to the base end of the drive motor assembly 124 such that the force sensor 126 reacts when it bears against the motor support cap 128. In another implementation, the force sensor 126 is affixed to the housing end cap 114 such that the force sensor 126 reacts when the drive motor assembly 124 bears against the force sensor 126. This configuration and arrangement of the drive motor assembly 124 and the force sensor 126 allows the force sensor 126 to react to forces imparted thereto by the drive motor assembly 124 and/or forces imparted to the drive motor assembly 124 via the fluid pressure of the fluid reservoir 111, i.e., the fluid located in the internal volume 180 of the fluid reservoir 111.

The drive motor assembly 124 includes an electric motor 136 that is actuated and controlled by the electronics module of the fluid infusion device 100. The motor 136 may be realized as a stepper motor that rotates in a stepwise or discrete manner corresponding to the desired number of fluid delivery strokes. Alternatively, the motor 136 could be a DC motor, a solenoid, or the like. The motor 136 may optionally include an encoder (not shown), which cooperates with the electronics module of the fluid infusion device 100 to monitor the number of motor rotations or portions thereof. This in turn can be used to accurately determine the position of the piston 400, thus providing information relating to the amount of fluid dispensed from the fluid reservoir 111.

The drive motor assembly 124 can be mounted in the housing 112 using an appropriate mounting feature, structure, or element. Alternatively, the mounting could be accomplished using a shaft bearing and leaf spring or other known compliance mountings.

The illustrated embodiment of the drive motor assembly 124 includes a drive member (such as the externally threaded drive gear or drive screw 125) that engages a second drive member (such as the piston 400) having a distal end 410. The distal end 410 may be attached to or integrated with the piston 400, as depicted in FIG. 2 and FIG. 3. The piston 400 is sized to fit within the internal volume 180 of the fluid reservoir 111, which enables the piston 400 to operatively cooperate with the fluid reservoir 111. The fluid reservoir 111 includes a plunger or stopper 300 located in the internal volume 180 of the fluid reservoir 111 and that includes at least one sealing element or feature (e.g., one or more O-rings, integral raised ridges, or a washer) for forming a fluid and air tight seal with the inner wall of the fluid reservoir 111. As mentioned previously, the fluid reservoir 111 is secured into the housing 112 with the fitting 110, which also serves as the interface between the fluid reservoir 111 and the infusion set tubing 108. For this embodiment, the stopper 300 is in contact with a linear actuation member, such as the piston 400. For example, the stopper 300 has a cavity 310 that receives the distal end 410 carried by the piston 400. The cavity 310 of the stopper 300 is positioned at the proximal end face of the stopper 300, and it is sized to receive and accommodate the distal end 410 of the piston 400. As described below in relation to FIGS. 4-6, FIGS. 7-10, FIGS. 11-14, and FIGS. 15-18, embodiments are provided herein to maintain engagement of the stopper 300 to the piston 400 so that the stopper 300 does not slip forward or otherwise reduce the volume of fluid in the fluid reservoir 111 without measured and controlled movement of the piston 400.

Referring to FIG. 3, measured and controlled movement of the piston 400 is provided through rotation of the drive shaft of the motor 136. Such rotation results in corresponding rotation of the drive screw 125, which in turn drives the piston 400 via the threaded engagement. Thus, rotation of the drive screw 125 results in axial (linear along the axis) displacement of the piston 400 and axial (linear along the axis) displacement of the piston distal end 410. Such linear displacement of the piston distal end 410 moves the stopper 300 (upward in FIG. 3) to deliver a predetermined or commanded amount of medication or liquid from the fluid infusion device 100. In this manner, the drive motor assembly 124 is configured to regulate delivery of fluid by actuating the stopper 300 (under the control of the electronics module and/or control system of the fluid infusion device 100). As described above, if a stepper motor is employed, then the drive motor assembly 124 can regulate delivery of fluid from the fluid infusion device 100 in discrete actuation or delivery strokes. The fluid infusion device 100 can employ the sleeve 120 or an equivalent feature (such as an anti-rotation key) to inhibit rotation of the drive motor assembly 124, which might otherwise result from torque generated by the motor 136. In some embodiments, the drive shaft of the drive motor assembly 124, the drive screw 125, and the piston 400 are all coaxially centered within the longitudinal axis of travel of the stopper 300. In certain alternative embodiments, one or more of these components may be offset from the center of the axis of travel and yet remain aligned with the axis of travel, which extends along the length of the fluid reservoir 111.

As mentioned above, certain embodiments of the fluid infusion device 100 accommodate removable and replaceable fluid reservoirs. When the piston 400 and, therefore, the stopper 300 of the fluid reservoir 111 are in their fully extended positions, the stopper 300 has forced most, if not all, of the fluid out of the fluid reservoir 111. After the stopper 300 has reached the end of its travel path, indicating that the fluid reservoir 111 has been depleted, the fluid reservoir 111 may be removed such that the stopper cavity 310 disengages from the distal end 410 of the piston 400. After the empty (or otherwise used) fluid reservoir 111 is removed, the electronics module or control system of the fluid infusion device 100 initiates a rewind operation during which the motor 136 rotates in the reverse direction to rewind the piston 400 back to its fully retracted position. Thereafter, a new or refilled fluid reservoir 111 can be installed, seated, and primed for use. In this regard, an embodiment provides for advancement of the piston 400 upon the insertion of a fluid reservoir 111 into the housing 112.

Although the illustrated embodiment employs a coaxial or inline drive system, alternative configurations could be utilized. For example, a drive system that uses a lead screw, a drive nut, and actuation arms (of the type described in U.S. Pat. No. 6,485,465) may be employed, with the force sensor 126 positioned in an appropriate location. In various embodiments, the drive train might include one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. Moreover, although the illustrated embodiment employs a sensor positioned at the end of the fluid drive train, other arrangements could be deployed. For example, a sensor could be placed at or near the front end of the fluid drive train.

The piston 400 advances until its distal end 410 comes into contact with the stopper 300 of the fluid reservoir 111. In operation, the force sensor 126 may be used to determine when the piston 400 contacts the stopper 300, and/or when the fluid reservoir 111 has been primed and is ready to deliver measured doses of fluid.

In particular embodiments, the force sensor 126 is used to detect when the piston 400 contacts the stopper 300. Thus, after the fluid reservoir 111 is placed into the fluid infusion device 100, the motor 136 is activated to move the piston 400 toward the fluid reservoir 111 to engage the stopper 300. In this regard, when a shoulder region 150 (see FIG. 3) of the piston 400 first contacts the stopper 300, the electronics module detects an increase in force imparted to the force sensor 126. The measured force continues to increase as the motor 136 continues to drive forward, in response to the fluid resistance in the fluid reservoir 111. When the piston 400 is properly seated with the stopper 300, the measured force increases to the seating threshold level. During the seating operation, if the measured force exceeds this seating threshold, the motor 136 is stopped until further commands are issued. The seating threshold is generally about 1.5 pounds. In alternative embodiments, higher or lower seating thresholds may be used depending on the force required to mate the piston 400 with the stopper 300, the force required to urge fluid from the fluid reservoir 111, the speed of the motor 136, the accuracy and resolution of the force sensor 126, or the like.

Figure 4:
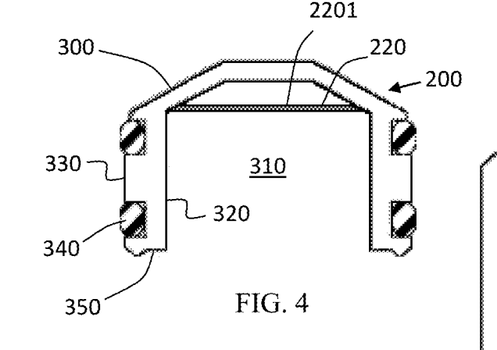
FIGS. 4, 5 and 6 are cross sectional and schematic representations of the stopper, piston and engagement of the stopper and piston respectively, of the fluid infusion device shown in FIG. 3, according to a first embodiment herein.
Figure 5:
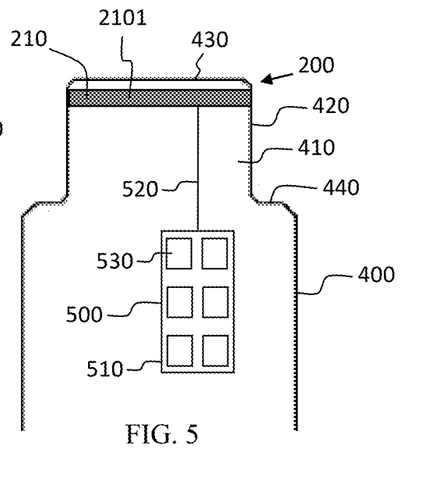
Figure 6:
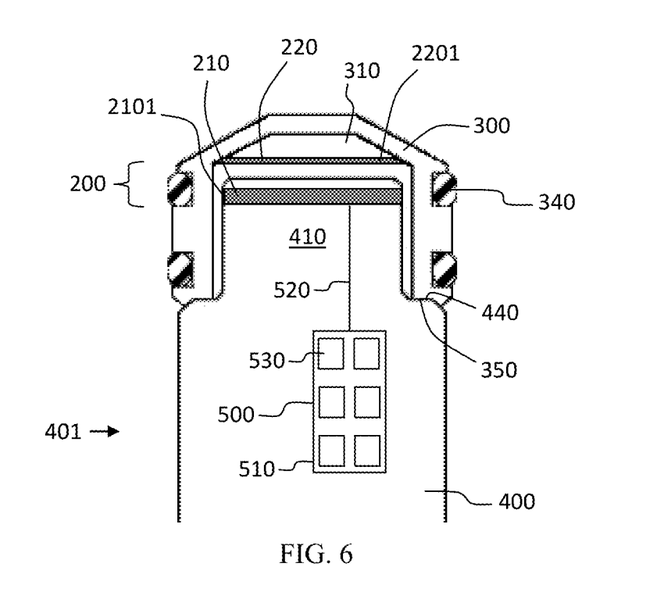

FIGS. 4-6 illustrate an embodiment in which engagement of the stopper 300 to the piston 400 is maintained by a coupling structure or element 200 so that the stopper 300 does not slip forward or otherwise reduce the volume of fluid in the fluid reservoir 111 without the measured and controlled movement of the piston 400. FIG. 4 illustrates an exemplary embodiment of the stopper 300. As shown, the stopper 300 is formed with an internal cavity 310 that is bounded by an internal sidewall surface 320. In certain embodiments, the internal sidewall surface 320 may be cylindrical or other annular shape. As further shown, the stopper 300 has an external or outer surface 330, which may also be cylindrical or another annular shape. Sealing mechanisms 340, such as O-rings may be provided at the outer surface 330 to provide for sealed contact with the fluid reservoir 111. As shown, the outer surface 330 and internal sidewall surface 320 extend downward to a proximal end 350 of the stopper.

FIG. 5 illustrates an exemplary embodiment of the piston 400. Piston 400 includes a distal end 410 for receipt within the stopper cavity 310. As shown, the piston 400 has an outer side surface 420 and a distal surface 430. Piston 400 is formed with a shoulder 440 that extends radially outward from the distal end 410.

As further shown in FIGS. 4 and 5, the stopper 300 and piston 400 are provided with a coupling structure 200. Specifically, the coupling structure 200 includes a first coupling component 210 and a second coupling component 220. In the embodiments of FIGS. 4 and 5, the first coupling component 210 is mounted or otherwise fixed to the distal end 410 of the piston and the second coupling component 220 is mounted or otherwise fixed to the stopper 300. In an exemplary embodiment, first coupling component 210 is a magnetic coupling component 2101 and second coupling component 220 is a second magnetic coupling component 2201, such as a magnet or a material attracted to a magnet. In certain embodiments, each magnetic coupling component 2101 and 2201 is a magnet.

As shown in FIG. 5, a sensor 500 is further provided. An exemplary sensor 500 may include a computing system 510 that is connected directly to the first coupling component 210 by a lead 520. In certain embodiments, the computing system 510 may not be directly connected to the first coupling component 210. The computing system 510 includes components 530 sufficient for operation, such as a circuit board, an electronics module (which may include or cooperate with one or more processors, processing modules, controllers, state machines, or the like); a power supply such as a battery or a battery pack; and other infusion pump hardware, software, and applications. The elements of the sensor 500 may be coupled together via an interconnection architecture or arrangement that facilitates transfer of data, commands, power, etc.

In an exemplary embodiment, the sensor 500 is mounted to the piston 400 to detect the strength of the magnetic field at or near the first coupling component 210. The sensor 500 may be programmed by engaging the piston 400 with the stopper 300 and measuring the resulting magnetic field. Thereafter, the sensor 500 may register engagement between the piston 400 and the stopper 300 when the magnetic field is measured at the same resulting magnetic field, or within a margin of error of the same resulting magnetic field.

FIG. 6 illustrates the stopper 300 of FIG. 4 and piston 400 of FIG. 5 after the piston 400 is advanced into the stopper cavity 310 and into engagement with the stopper 300. As shown, the coupling structure 200 includes the first coupling component 210 (first magnetic coupling component 2101) and the second coupling component 220 (second magnetic coupling component 2201). In this embodiment, engagement is obtained by positioning the two magnetic coupling components 2101 and 2201 near enough to one another to cause magnetic attraction sufficient to prevent an unintended movement of the stopper 300 away from the piston 400. As shown, the piston 400 may further engage and advance the stopper 300 through physical contact, such as between the shoulder 440 of the piston 400 and the proximal end 350 of the stopper 300, though such contact would not prevent movement of the stopper 300 away from the piston 400.

In the embodiment of FIGS. 4-6, the sensor 500 may monitor whether the first coupling component 210 and second coupling component 220 move away from one another as an indication of forward movement of the stopper 300, and may communicate a signal or alert if such movement occurs.

Figures 7, 8:
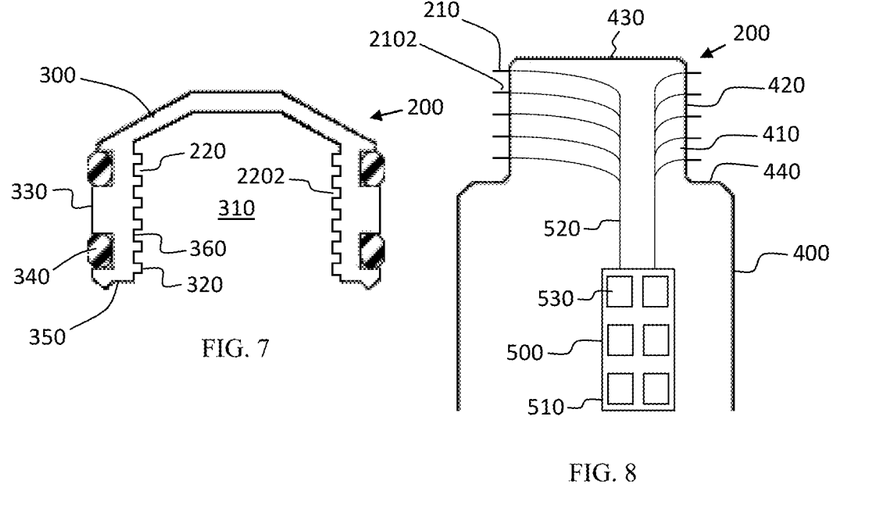
FIGS. 7, 8 and 10 are cross sectional and schematic representations of the stopper, piston and engagement of the stopper and piston respectively, of the fluid infusion device shown in FIG. 3, according to a second embodiment herein.

FIGS. 7-10 illustrate another embodiment in which engagement of the stopper 300 to the piston 400 is maintained by a coupling structure 200 so that the stopper 300 does not slip forward or otherwise reduce the volume of fluid in the fluid reservoir 111 without the measured and controlled movement of the piston 400. FIG. 7 illustrates an exemplary embodiment of the stopper 300. As shown, the stopper 300 is formed with an internal cavity 310 that is bounded by an internal sidewall surface 320. In certain embodiments, the internal sidewall surface 320 may be cylindrical or other annular shape. As further shown, the stopper 300 has an external or outer surface 330, which may also be cylindrical or another annular shape. Sealing mechanisms 340, such as O-rings may be provided at the outer surface 330 to provide for sealed contact with the fluid reservoir 111. As shown, the outer surface 330 and internal sidewall surface 320 extend downward to a proximal end 350 of the stopper.

FIG. 8 illustrates an exemplary embodiment of the piston 400. Piston 400 includes a distal end 410 for receipt within the stopper cavity 310. As shown, the piston 400 has an outer side surface 420 and a distal surface 430. Piston 400 is formed with a shoulder 440 that extends radially outward from the distal end 410.

As further shown in FIGS. 7 and 8, the stopper 300 and piston 400 are provided with a coupling structure 200. Specifically, the coupling structure 200 includes a first coupling component 210 and a second coupling component 220. In the embodiments of FIGS. 7 and 8, the first coupling component 210 is mounted or otherwise fixed to the distal end 410 of the piston and the second coupling component 220 is mounted or otherwise fixed to the stopper 300. In an exemplary embodiment, each coupling component 210 and 220 is provided for reciprocal mechanical connection.

Figure 9:
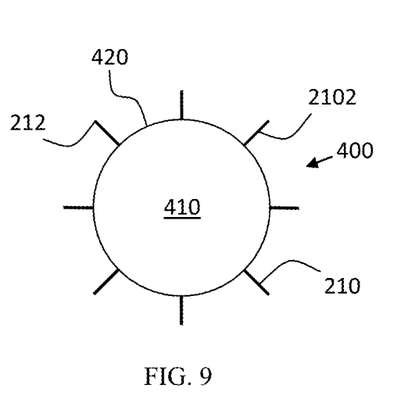
FIG. 9 is a plan view of the distal end of the piston of FIG. 8.

Specifically, the first coupling component 210 is a first mechanical coupling component 2102 in the form of a radially outward extending wing or projection, or a plurality of wings or projections, that extends radially out from the outer side surface 420 of the distal end 410 of the piston 400 and that is deflectable in an axial or circumferential direction. FIG. 9 provides an end view of the distal end 410 of the piston 400 to illustrate that projections 2102 may be circumferentially spaced about the outer side surface 420. Further, each projection 2102 extends from the outer side surface 420 of the distal end 410 of the piston 400 to a radially distal end 212. In an exemplary embodiment, the projections 2102 are sufficiently flexible to allow the radially distal ends 212 to be deflected axially and/or circumferentially and are sufficiently resilient to return to the radially extending orientation of the projections 2102 shown in FIG. 9.

As shown in FIG. 7, the second coupling component 220 is a second mechanical coupling component 2202 in the form of a recess, or a plurality of recesses, that extends radially outward from the internal sidewall surface 320 of the stopper 300 to a recessed surface 360. The recess 2202 may be formed as a continuous thread formed on the internal sidewall surface 320 of the stopper 300.

As shown in FIG. 8, a sensor 500 is further provided. An exemplary sensor 500 may include a computing system 510 that is connected directly to the first coupling component 210 by a lead 520. In certain embodiments, the computing system 510 may not be directly connected to the first coupling component 210. The computing system 510 includes components 530 sufficient for operation, such as a circuit board, an electronics module (which may include or cooperate with one or more processors, processing modules, controllers, state machines, or the like); a power supply such as a battery or a battery pack; and other infusion pump hardware, software, and applications. The elements of the sensor 500 may be coupled together via an interconnection architecture or arrangement that facilitates transfer of data, commands, power, etc.

In an exemplary embodiment, the sensor 500 is mounted to the piston 400 to detect the flexural stress in the radial projection or projections 2102. For example, the sensor 500 may be a pressure sensor. The sensor 500 may be programmed by engaging the piston 400 with the stopper 300 and measuring the resulting pressure indicative of flexural stress in the radial projection or projections 2102. Thereafter, the sensor 500 may register engagement between the piston 400 and the stopper 300 when the flexural stress or pressure is measured at the same measured level, or within a margin of error of the same measured level.

Figure 10:
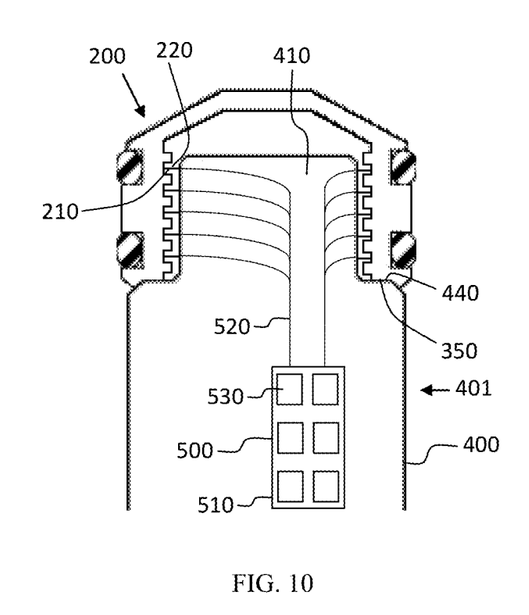

FIG. 10 illustrates the stopper 300 of FIG. 7 and piston 400 of FIG. 8 after the piston 400 is advanced into the stopper cavity 310 and into engagement with the stopper 300. As shown, the coupling structure 200 includes the first coupling component 210 (first mechanical coupling component 2102) and the second coupling component 220 (second mechanical coupling component 2202). In this embodiment, engagement is obtained by passing projections 2102 past the proximal end 350 such that projections 2102 are deflected downward (in the frame of reference of FIG. 10) by the internal sidewall surface 320. When the radially distal end 212 of each projection 2102 reaches a recess 2202 and clears the internal sidewall surface 320, the projection 2102 flexes back to the radially extending orientation of FIG. 10. Thus, after the piston 400 is located at the desired position 401, the projections 2102 will register any added pressure from contact with the internal sidewall surface 320 caused by removing the projections 2102 from the recesses 2202, such as when the stopper 300 advances distally from the piston 400. As shown, the piston 400 may further engage and advance the stopper 300 through physical contact, such as between the shoulder 440 of the piston 400 and the proximal end 350 of the stopper 300, though such contact would not prevent movement of the stopper 300 away from the piston 400.

In the embodiment of FIGS. 7-10, the sensor 500 may monitor whether the first coupling component 210 and second coupling component 220 become disengaged as an indication of forward movement of the stopper 300, and may communicate a signal or alert if such movement occurs.

Figure 11:
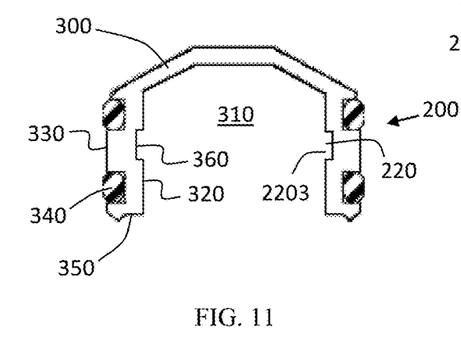
FIGS. 11, 12, 13 and 14 are cross sectional and schematic representations of the stopper, piston, near engagement and engagement of the stopper and piston respectively, of the fluid infusion device shown in FIG. 3, according to a third embodiment herein.

FIGS. 11-14 illustrate another embodiment in which engagement of the stopper 300 to the piston 400 is maintained by a coupling structure 200 so that the stopper 300 does not slip forward or otherwise reduce the volume of fluid in the fluid reservoir 111 without the measured and controlled movement of the piston 400. FIG. 11 illustrates an exemplary embodiment of the stopper 300. As shown, the stopper 300 is formed with an internal cavity 310 that is bounded by an internal sidewall surface 320. In certain embodiments, the internal sidewall surface 320 may be cylindrical or other annular shape. As further shown, the stopper 300 has an external or outer surface 330, which may also be cylindrical or another annular shape. Sealing mechanisms 340, such as O-rings may be provided at the outer surface 330 to provide for sealed contact with the fluid reservoir 111. As shown, the outer surface 330 and internal sidewall surface 320 extend downward to a proximal end 350 of the stopper.

Figure 12:
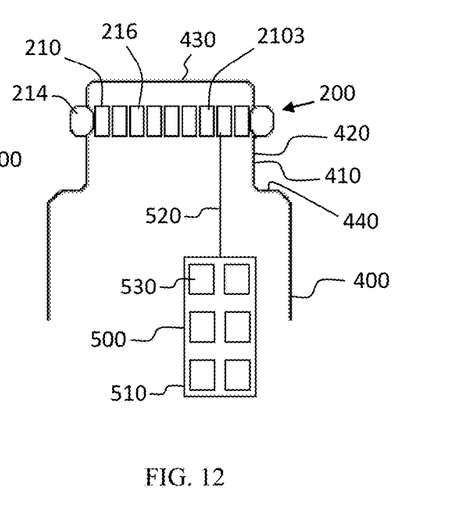

FIG. 12 illustrates an exemplary embodiment of the piston 400. Piston 400 includes a distal end 410 for receipt within the stopper cavity 310. As shown, the piston 400 has an outer side surface 420 and a distal surface 430. Piston 400 is formed with a shoulder 440 that extends radially outward from the distal end 410.

As further shown in FIGS. 11 and 12, the stopper 300 and piston 400 are provided with a coupling structure 200. Specifically, the coupling structure 200 includes a first coupling component 210 and a second coupling component 220. In the embodiments of FIGS. 11 and 12, the first coupling component 210 is mounted or otherwise fixed to the distal end 410 of the piston and the second coupling component 220 is mounted or otherwise fixed to the stopper 300. In an exemplary embodiment, each coupling component 210 and 220 is provided for reciprocal mechanical connection.

Specifically, the first coupling component 210 is a first mechanical coupling component 2103 in the form of a radially-biased projection, or a plurality of projections, that is extendable from, and retractable into, the outer side surface 420 of the distal end 410 of the piston 400. An exemplary radially-biased projection 2103 is a spring-loaded ball valve or spring-loaded ball element that includes a ball or rounded nose end 214. The end 214 is biased outward from the outer side surface 420 of the distal end 410 of the piston 400 by a spring or other biasing element 216. In certain embodiments and as shown in FIG. 12, the biasing element 216 may extend through the distal end 410 of the piston 400 between two opposite ends 214 that are each biased outward from the outer side surface 420 of the distal end 410 of the piston 400.

As shown in FIG. 11, the second coupling component 220 is a second mechanical coupling component 2203 in the form of a recess, or a plurality of recesses, that extends radially outward from the internal sidewall surface 320 of the stopper 300 to a recessed surface 360. The recess 2203 may be formed as a continuous annular recess around the internal sidewall surface 320 of the stopper 300.

As shown in FIG. 12, a sensor 500 is further provided. An exemplary sensor 500 may include a computing system 510 that is connected directly to the first coupling component 210 by a lead 520. In certain embodiments, the computing system 510 may not be directly connected to the first coupling component 210. The computing system 510 includes components 530 sufficient for operation, such as a circuit board, an electronics module (which may include or cooperate with one or more processors, processing modules, controllers, state machines, or the like); a power supply such as a battery or a battery pack; and other infusion pump hardware, software, and applications. The elements of the sensor 500 may be coupled together via an interconnection architecture or arrangement that facilitates transfer of data, commands, power, etc.

In an exemplary embodiment, the sensor 500 is mounted to the piston 400 to detect the tension in the biasing element 216. For example, the sensor 500 may be a pressure sensor. The sensor 500 may be programmed by engaging the piston 400 with the stopper 300 and measuring the resulting pressure indicative of tension in the biasing element 216. Thereafter, the sensor 500 may register engagement between the piston 400 and the stopper 300 when the flexural stress or pressure is measured at the same measured level, or within a margin of error of the same measured level.

Figure 13:
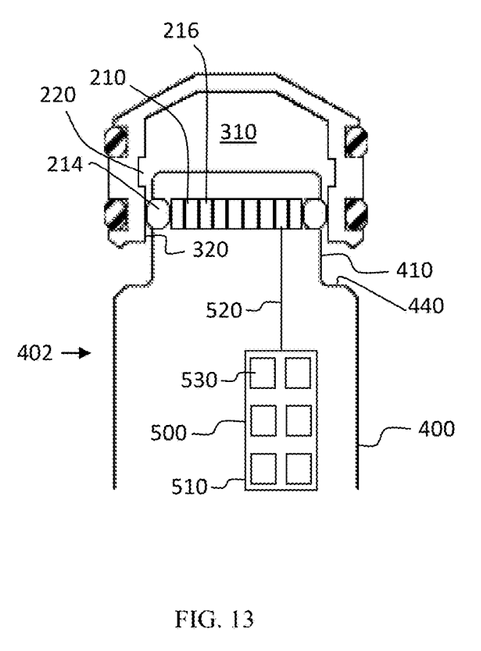
Figure 14:
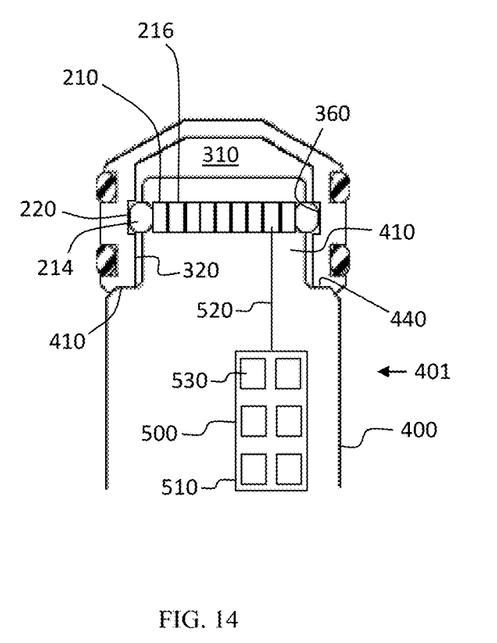

FIGS. 13 and 14 illustrate that the coupling structure 200 includes the first coupling component 210 (first mechanical coupling component 2103) and the second coupling component 220 (second mechanical coupling component 2203). FIG. 13 illustrates the stopper 300 of FIG. 11 and piston 400 of FIG. 12 after the piston 400 is advanced into the stopper cavity 310 but before the piston 400 engages the stopper 300, at an intermediate position 402. As shown, the ends 214 of the radially-biased projections 2103 are retracted into the distal end 410 of the piston 400 due to contact with the internal sidewall surface 320 of the stopper 300. As a result, tension in the biasing element 216 is increased.

FIG. 14 illustrates the further advancement of the piston 400 from the intermediate position 402 to the desired position 401 where the piston 400 and stopper 300 are engaged with one another. In this embodiment, engagement is obtained by extending the ends 214 into the recesses 2203. After the ends 214 are extended into the recesses 2203, tension in the biasing element 216 is decreased. Thus, after the piston 400 is located at the desired position 401, the biased projections 2103 will register any added pressure from retraction into the distal end 410 of piston 400 due to contact with the internal sidewall surface 320 caused by removing the projections 2102 from the recesses 2202, such as when the stopper 300 advances distally from the piston 400. As shown, the piston 400 may further engage and advance the stopper 300 through physical contact, such as between the shoulder 440 of the piston 400 and the proximal end 350 of the stopper 300, though such contact would not prevent movement of the stopper 300 away from the piston 400.

In the embodiment of FIGS. 11-14, the sensor 500 may monitor whether the first coupling component 210 and second coupling component 220 become disengaged as an indication of forward movement of the stopper 300, and may communicate a signal or alert if such movement occurs.

Figure 15:
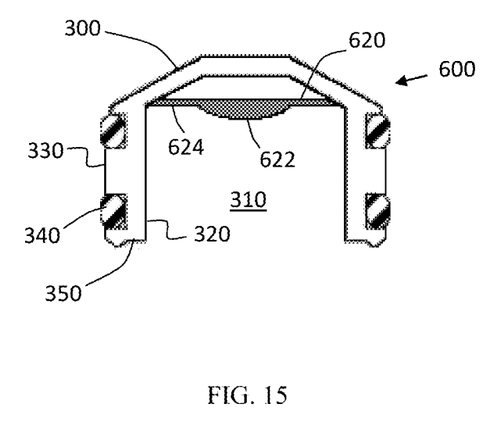
FIGS. 15, 16 and 17 are cross sectional and schematic representations of the stopper, piston and sensing of contact between the stopper and piston respectively, of the fluid infusion device shown in FIG. 3, according to a fourth embodiment herein.
Figure 16:
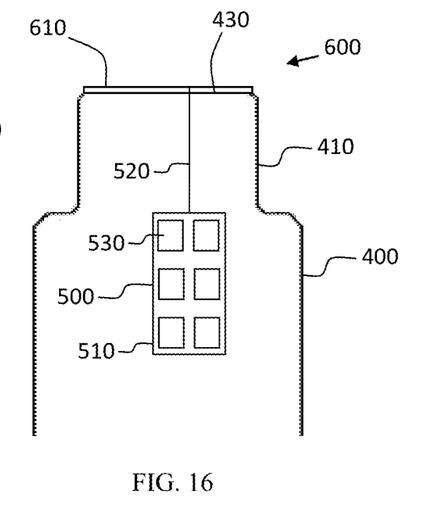
Figure 17:
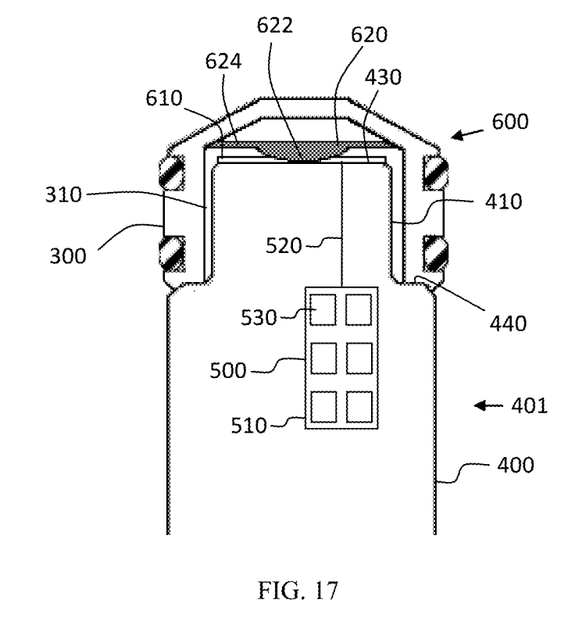

While the embodiments of FIGS. 4-6, 7-10, and 11-14 each include a sensing capability resulting from the described coupling structures 200, each may be provided with an alternative or additional sensing arrangement. For example, FIGS. 15-17 illustrate another embodiment in which engagement of the stopper 300 to the piston 400 is sensed by a sensor 500 to monitor whether the stopper 300 has slipped forward or otherwise reduced the volume of fluid in the fluid reservoir 111 without the measured and controlled movement of the piston 400. FIG. 15 illustrates an exemplary embodiment of the stopper 300. As shown, the stopper 300 is formed with an internal cavity 310 that is bounded by an internal sidewall surface 320. In certain embodiments, the internal sidewall surface 320 may be cylindrical or other annular shape. As further shown, the stopper 300 has an external or outer surface 330, which may also be cylindrical or another annular shape. Sealing mechanisms 340, such as O-rings may be provided at the outer surface 330 to provide for sealed contact with the fluid reservoir 111. As shown, the outer surface 330 and internal sidewall surface 320 extend downward to a proximal end 350 of the stopper.

FIG. 16 illustrates an exemplary embodiment of the piston 400. Piston 400 includes a distal end 410 for receipt within the stopper cavity 310. As shown, the piston 400 has an outer side surface 420 and a distal surface 430. Piston 400 is formed with a shoulder 440 that extends radially outward from the distal end 410.

As further shown in FIGS. 15 and 16, the stopper 300 and piston 400 are provided with a sensing structure 600 coupled to the sensor 500. Specifically, the sensing structure 600 includes a first sensing component 610 and a second sensing component 620. In the embodiments of FIGS. 15 and 16, the first sensing component 610 is mounted or otherwise fixed to the distal end 410 of the piston and the second sensing component 620 is mounted or otherwise fixed to the stopper 300. In an exemplary embodiment, each sensing component 610 and 620 is provided for reciprocal mechanical contact.

Specifically, the first sensing component 610 is a touch pad or similar component that registers contact with another object, such as through electric field proximity sensing or through capacitive sensing. In certain embodiments and as shown in FIG. 16, the first sensing component 610 is located on the distal surface 430 of the distal end 410 of the piston 400.

As shown in FIG. 15, the second sensing component 620 includes an axial projection 622 that extends downward (in the frame of reference of FIG. 15) into the cavity 310 of the stopper 300. The axial projection 622 may be supported by a web 624 that is connected to the internal sidewall surface 320. In exemplary embodiments, the axial projection 622 and web 624 are integral and may be formed from a flexible material, such as a rubber or thermoplastic material.

FIG. 16 illustrates that an exemplary sensor 500 may include a computing system 510 that is connected directly to the first sensing component 610 by a lead 520. In certain embodiments, the computing system 510 may not be directly connected to the first sensing component 610. The computing system 510 includes components 530 sufficient for operation, such as a circuit board, an electronics module (which may include or cooperate with one or more processors, processing modules, controllers, state machines, or the like); a power supply such as a battery or a battery pack; and other infusion pump hardware, software, and applications. The elements of the sensor 500 may be coupled together via an interconnection architecture or arrangement that facilitates transfer of data, commands, power, etc.

In an exemplary embodiment, the sensor 500 is mounted to the first sensing component 610 to detect contact between the second sensing component 620 and the first sensing component 610. For example, the sensor 500 may be an electrostatic sensor.

FIG. 17 illustrates the advancement of the piston 400 to the desired position 401 where the piston 400 contacts the stopper 300. In this embodiment, the axial projection 622 of the second sensing component 620 contacts the first sensing component 610. For a first sensing component 610 utilizing electric field proximity sensing, the contact with the axial projection 622 causes a change in the electrostatic field around the first sensing component 610. This change is monitored by the sensor 500 and is indicative of contact between the piston 400 and stopper 300. If the stopper 300 advances out of contact with the piston 400, contact between the axial projection 622 and first sensing component 610 is interrupted and the electrostatic field around the first sensing component 610 changes. As a result, the sensor 500 may monitor whether the first sensing component 610 and second sensing component 620 are in contact, and may communicate a signal or alert if sensing components 610 and 620 lose contact as an indication of forward movement of the stopper 300.

As mentioned previously, the fluid infusion device 100 is suitably configured to support a number of techniques, processes, and methodologies that utilize the coupling structure 200 and/or sensing structure 600. In practice, the fluid infusion device 100 includes an electronics module, processing logic, software applications, and/or other features that are used to carry out the various operating processes described here.

Figure 18:
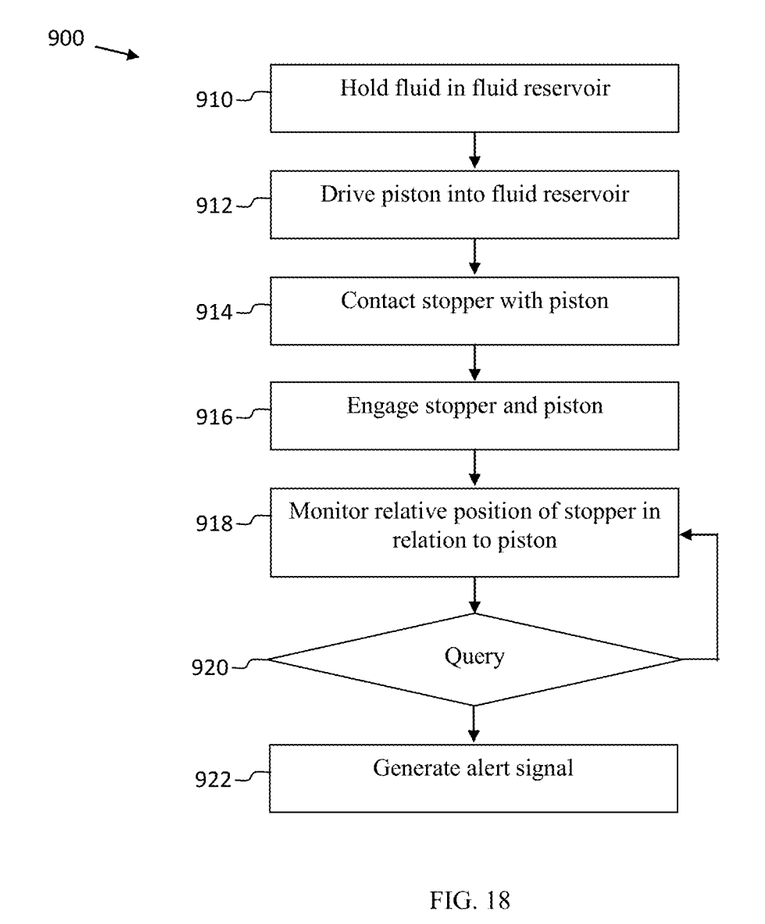
FIG. 18 is a flow chart illustrating a method for operating a fluid delivery device in accordance with an embodiment herein.

FIG. 18 illustrates a method 900 for operating a fluid infusion device such as described above. As shown, the method 900 includes holding a fluid in an internal volume of a fluid reservoir partially bounded by a stopper positioned in the internal volume at action block 910. At action block 912, the method includes driving a piston into the internal volume of the fluid reservoir. Further, action block 914 includes contacting the stopper with the piston Action block 916 is the optional action of engaging the stopper and the piston. Such engagement may be through mechanical or magnetic coupling components as described above. In other embodiments, the stopper and piston may not be engaged by coupling components, but rather may be simply contacted to one another.

In either embodiment, the method 900 continues at action block 918 with monitoring a relative position of the stopper in relation to the piston with a sensor to determine whether the stopper moves out of contact with the piston. This action block presents query 920 which asks whether the stopper has lost contact with the piston. If the stopper remains in contact with the piston, then the method continues monitoring at action block 918. If the stopper has advanced out of contact with the piston, then at action block 922 the method 900 generates an alert signal. As a result, the user is aware that the volume of fluid in the reservoir may not be accurately represented by the indicated position of the piston and that the device may need to be reset by advancement of the piston or other remedial action.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A device for delivering fluid to a user, the device comprising:
    a fluid reservoir for holding the fluid, the fluid reservoir defining an internal volume and a stopper positioned in the internal volume of the fluid reservoir, wherein the stopper is formed with a cavity;
    a piston having a distal end received within the cavity of the stopper;
    an actuator coupled to the piston for driving the piston into the internal volume of the fluid reservoir;
    a coupling device for engaging the piston in the cavity of the stopper at a desired position; and a sensor for measuring information indicative of axial separation of the stopper from the piston.

2. The device of claim 1 wherein the coupling device is a magnetic coupling device and includes a first component mounted to the stopper and a second component mounted to the piston.

3. The device of claim 2 wherein the sensor is coupled to the second component and is configured to detect magnetic field strength.

4. The device of claim 1 wherein the stopper has an inner sidewall surface, wherein the piston has an outer surface, and wherein the coupling device comprises a recess formed in the inner sidewall surface and a flexible wing extending outward from the outer surface of the piston and configured to extend into the recess and engage with the inner sidewall surface of the stopper.

5. The device of claim 4 wherein the sensor is coupled to the flexible wing and is configured to detect deflection pressure on the flexible wing.

6. The device of claim 1 wherein the stopper has an inner sidewall surface, and wherein the coupling device comprises a recess formed in the inner sidewall surface and a spring-loaded ball element mounted to the piston and configured to extend into the recess and engage with the inner sidewall surface of the stopper.

7. The device of claim 6 wherein the sensor is coupled to the spring-loaded ball element and is configured to detect spring tension on the spring-loaded ball element.

8. The device of claim 1 wherein the sensor comprises:
   a projection mounted to the stopper and extending into the cavity of the stopper; and
   a pressure sensor mounted to the piston, wherein the projection contacts the pressure sensor when the piston is engaged in the cavity of the stopper at the desired position.

9. The device of claim 8 wherein the pressure sensor comprises an electric field proximity sensor.

10. A device for detecting whether a fluid delivery device stopper is correctly positioned, the device comprising:
    a fluid reservoir for holding fluid, the fluid reservoir defining an internal volume wherein the fluid delivery device stopper is positioned, wherein the fluid delivery device stopper is formed with a cavity;
    a piston having a distal end received within the cavity of the fluid delivery device stopper;
    an actuator coupled to the piston for driving the piston into the internal volume of the fluid reservoir; and
    a sensor for measuring information indicative of axial separation of the fluid delivery device stopper from the piston.

11. The device of claim 10 wherein the sensor includes a first magnetic component mounted to the fluid delivery device stopper and a second magnetic component mounted to the piston.

12. The device of claim 11 wherein the sensor is configured to detect magnetic field strength.

13. The device of claim 10 wherein the piston has an outer surface and a flexible wing extending outward from the outer surface of the piston and configured to contact the fluid delivery device stopper, and wherein the sensor is coupled to the flexible wing and is configured to detect deflection pressure on the flexible wing.

14. The device of claim 10 wherein a spring-loaded ball element is mounted to the piston, and wherein the sensor is coupled to the spring-loaded ball element and is configured to detect spring tension on the spring-loaded ball element.

15. The device of claim 10 wherein the sensor comprises:
    a projection mounted to the fluid delivery device stopper and extending into the cavity of the fluid delivery device stopper; and
    a pressure sensor mounted to the piston, wherein the projection contacts the pressure sensor when the piston is engaged in the cavity of the fluid delivery device stopper.

16. The device of claim 15 wherein the pressure sensor comprises an electric field proximity sensor.

17. A method for operating a fluid infusion device comprising:
    holding a fluid in an internal volume of a fluid reservoir partially bounded by a stopper positioned in the internal volume, wherein the stopper is formed with a cavity;
    driving a piston into the internal volume of the fluid reservoir;
    contacting the stopper with the piston; and
    measuring information indicative of axial separation of the stopper the piston with a sensor to determine whether the stopper moves out of contact with the piston.

18. The method of claim 17 further comprising generating an alert signal from the sensor when the stopper moves out of contact with the piston.

19. The method of claim 17 further comprising mechanically engaging the stopper and the piston.

20. The method of claim 17 further comprising magnetically engaging the stopper and the piston.

* * * * *